United States Patent [19]

Mina et al.

[11] 3,975,394
[45] Aug. 17, 1976

[54] PROCESS FOR 2-MERCAPTOBENZOTHIAZOLE

[75] Inventors: George Louis Mina, Pennsville; John Erjavec, Phillipsburg, both of N.J.

[73] Assignee: American Cyanamid Company, Stamford, Conn.

[22] Filed: Nov. 14, 1974

[21] Appl. No.: 523,954

[52] U.S. Cl. ................................. 260/306
[51] Int. Cl.² ........................... C07D 277/72
[58] Field of Search ...................... 260/306

[56] References Cited
UNITED STATES PATENTS
1,753,898   4/1930   Merkle.............................. 260/306

Primary Examiner—Paul M. Coughlan, Jr.
Assistant Examiner—D. B. Springer
Attorney, Agent, or Firm—Charles J. Fickey

[57] ABSTRACT

A process for preparing 2-mercaptobenzothiazole is provided which comprises reacting benzothiazole with sulfur in a molar ratio of benzothiazole to sulfur in a range of from about 1:0.9 to 1:1.3 at a temperature of from about 200° to 260°C. for about 30 minutes to 3 hours.

6 Claims, No Drawings

PROCESS FOR 2-MERCAPTOBENZOTHIAZOLE

Generally stated, the subject matter of the present invention relates to the manufacture of 2-mercaptobenzothiazole. More particularly, the invention relates to a process in which benzothiazole is converted to 2-mercaptobenzothiazole by reaction with sulfur.

BACKGROUND OF THE INVENTION

The compound 2-mercaptobenzothiazole is a well known and extensively used thiazole accelerator for rubber. It is readily manufactured in high yield and purity by an autoclave reaction of aniline, sulfur and carbon disulfide. Benzothiazole is a by-product in the manufacture of 2-mercaptobenzothiazole and is generally separated from the 2-mercaptobenzothiazole autoclave "melt" by steam distillation.

The use of 2-mercaptobenzothiazole as such and in the form of derivatives, such as sulfenamide accelerators, is growing in direct proportion with the rubber industry. The present processes employed to prepare 2-mercaptobenzothiazole are relatively satisfactory in terms of yield; however, for obvious reasons the complete conversion to 2-mercaptobenzothiazole would be highly desirable. Therefore, the conversion of benzothiazole to 2-mercaptobenzothiazole would present a significant improvement in the art accepted processes for preparing 2-mercaptobenzothiazole.

The present invention represents the culmination of a long series of investigations, conducted largely by the inventors, directed to finding a process for preparing 2-mercaptobenzothiazole from benzothiazole.

Accordingly, it is a primary object of the present invention to find a process for preparing 2-mercaptobenzothiazole from benzothiazole.

It is yet another object of the invention to find a new process for preparing 2-mercaptobenzothiazole using the benzothiazole by-product of the conventional process for preparing 2-mercaptobenzothiazole.

Additional objects and advantages will be set forth in part in the description which follows and in part will be obvious from the description which follows or may be learned by the practice of the invention, the objects and advantages being realized and attained by means of the compositions, processes and improvements, particularly pointed out in the appended claims.

THE INVENTION

To achieve the foregoing objects and in accordance with its purpose as embodied and broadly described, the present invention provides a process for preparing 2-mercaptobenzothiazole which comprises reacting 1 molar proportion of benzothiazole with from about 0.9 to 1.3 molar proportions of sulfur at a temperature of from about 220° to 260°C. for about 30 minutes to 3 hours.

It is to be understood that both the foregoing general description and the following detailed description are exemplory and explanatory and are not restrictive of the invention.

As part of an investigation to find new outlets for benzothiazole, it was found that an equilibrium probably exists between benzothiazole (BT) and 2-mercaptobenzothiazole (MBT), e.g.:

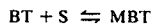

This is indicated by the formation of 2-mercaptobenzothiazole when benzothiazole and sulfur were heated in an autoclave for 1 to 2 hours at about 270°C. The reaction was accompanied by tar formation which increased with reaction time.

Continued exploration of the reaction has resulted in the discovery that benzothiazole can be readily converted into 2-mercaptobenzothiazole in very high yield by reaction with sulfur under certain reaction conditions.

In accordance with the present invention, benzothiazole and elemental sulfur are heated at atmospheric pressure to produce 2-mercaptobenzothiazole. The mole ratio of sulfur to benzothiazole in which the process will produce a high yield of 2-mercaptobenzothiazole is from about 0.9:1 to about 1.3:1, preferably 0.95:1 to 1.1:1, although satisfactory yields can be obtained at ratios slightly higher and lower.

The reaction occurs most readily in the temperature range of about 220°C. to about 260°C., preferably about 230° to 250°C., with optimum results at about 240°C, although lower temperatures, about 200°C., will also provide the desired product.

Reaction time varies with the temperature and mole ratio but ranges from about 30 minutes to 3 hours under the preferred conditions. A reaction time of at least one hour is preferred.

Although the present invention relates to the conversion of pure benzothiazole to 2-mercaptobenzothiazole in high yield, in practice it may be preferable to employ a crude benzothiazole, obtained when benzothiazole is steam distilled from the 2-mercaptobenzothiazole melt, as described above.

The crude benzothiazole contains as the principal contaminants aniline and thiocarbanilide, along with a small amount of water.

The aniline content of the crude benzothiazole is readily converted to 2-mercaptobenzothiazole by reaction with the appropriate amounts of sulfur and carbon disulfide, in accordance with the well known process for the manufacture of 2-mercaptobenzothiazole.

Additionally, it is known to convert thiocarbanilide to 2-mercaptobenzothiazole by a similar reaction with sulfur and carbon disulfide; see J. Chem. Ind., Japan, 46, 957–960 (1942).

Thus, it has been found that this crude benzothiazole may be incorporated as a starting material, or recycled, in the conventional autoclave reaction of aniline, sulfur and carbon disulfide to prepare 2-mercaptobenzothiazole, thereby utilizing the principal by-product in the manufacture of 2-mercaptobenzothiazole to produce additional amounts of 2-mercaptobenzothiazole.

While the principal 2-mercaptobenzothiazole process requires elevated temperature and pressure, it has been found that pressure has no effect on the conversion of benzothiazole to 2-mercaptobenzothiazole with sulfur, and that the conversion readily occurs under pressure. This pressure insensitivity readily permits the use of benzothiazole as an intermediate in the manufacture of 2-mercaptobenzothiazole.

The following examples are provided for illustrative purposes and may include particular features of the invention. However, the examples should not be construed as limiting the invention, many variations of which are possible without departing from the spirit or scope thereof.

EXAMPLE I

Pure benzothiazole (270.46 grams, 2.0 moles) and 72.35 grams of elemental sulfur (2.26 gram-atoms) were heated at atmospheric pressure at 240°C. A sample (14.7 grams) was removed after 203 minutes, stirred with 100 ml. 1N sodium hydroxide and 100 ml. water at 20°C. for 12 hours. The solution was filtered and the filtrate acidified with 2N sulfuric acid. The solid precipitate was filtered, washed with water and dried at 70°C. to give 13.27 grams of 2-mercaptobenzothiazole (91.4% yield, m.p. 177°–179°C., purity 90.2%).

EXAMPLE II

A sample of benzothiazole recovered from a 2-mercaptobenzothiazole "melt" had the following analysis:

| | |
|---|---|
| Benzothiazole | 78.4% |
| Aniline | 14.6% |
| Thiocarbanilide | 3.8% |
| Water | 3.2% |
| | 100.0% |

In accordance with the present invention and known processes for conversion of aniline and thiocarbanilide to 2-mercaptobenzothiazole, sulfur and carbon disulfide were charged to the autoclave as follows:

| Component | Moles per 100 Grams Recovered Benzothiazole | Added/100 Grams Moles S | Moles $CS_2$ |
|---|---|---|---|
| Benzothiazole | 0.580 | 0.655(a) | 0 |
| Aniline | 0.157 | 0.152(b) | 0.177(b) |
| Thiocarbanilide | 0.017 | 0.033(c) | 0.026(c) |
| Water | 0.178 | — | 0.089(d) |
| Total Moles | | 0.840 | 0.202 |
| Total Grams | | 26.940 | 22.230 |

Notes:
a. 1.13 moles sulfur/mole benzothiazole
b. 0.97 mole sulfur and 1.13 moles $CS_2$ per mole aniline
c. each thiocarbanilide equivalent to 2 aniline and 1 $CS_2$
$$\phi NH-\overset{S}{C}-NH-\phi + CS_2 + 2S \rightarrow 2MBT + H_2S$$
1.94 moles sulfur and 1.26 moles $CS_2$ used.
d. $2 H_2O + CS_2 \rightarrow CO_2 + 2H_2S$ To a 1.3 liter autoclave was added a total of 600 grams benzothiazole, 161.6 grams sulfur and 133.4 grams $CS_2$. After 3 hours reaction at 250°C./1100 psi maximum., the reaction mixture gave the following analysis:

| Component | Percent |
|---|---|
| 2-mercaptobenzothiazole | 85.53 |
| Benzothiazole | 5.16 |
| Aniline | 0.29 |
| Thiocarbanilide | 0.24 |
| Aminobenzenethiol | 0.31 |

EXAMPLE III

Pure benzothiazole was reacted with elemental sulfur in a ratio of 1 to 1.13 and a temperature of 240°C. The results at different time intervals are set forth in the following table:

| Reaction Time | 2-mercaptobenzothiazole Yield (%) |
|---|---|
| 140 min. | 92.26 |
| 180 min. | 91.33 |
| 203.5 min. | 91.52 |
| 240 min. | 90.70 |
| 300 min. | 89.34 |
| 360 min. | 89.40 |

What is claimed:
1. A process for preparing 2-mercaptobenzothiozole which comprises reacting benzothiazole with sulfur in a molar ratio of benzothiazole to sulfur in a range of from about 1:0.9 to 1:1.3 at a temperature of from about 200° to 260°C. for about 30 minutes to 3 hours.
2. The process according to claim 1 wherein the molar ratio of benzothiazole to sulfur is 1:0.95 to 1:1.1.
3. The process according to claim 1 wherein the temperature is from about 230° to 250°C.
4. The process according to claim 1 wherein the temperature is 240°C.
5. The process according to claim 1 wherein the process is carried out for at least about one hour.
6. The process according to claim 1 wherein the reaction is carried out under autogenous pressure.

* * * * *